(12) United States Patent
Abusbeih

(10) Patent No.: US 10,940,089 B2
(45) Date of Patent: Mar. 9, 2021

(54) MEDICATION CRUSHING, GRINDING, AND ADMINISTERING SYRINGE AND METHOD OF USE

(71) Applicant: Ghanem Abusbeih, St. Louis, MO (US)

(72) Inventor: Ghanem Abusbeih, St. Louis, MO (US)

( * ) Notice: Subject to any disclaimer, the term of this patent is extended or adjusted under 35 U.S.C. 154(b) by 127 days.

(21) Appl. No.: 15/982,227

(22) Filed: May 17, 2018

(65) Prior Publication Data

US 2018/0333332 A1 Nov. 22, 2018

Related U.S. Application Data

(60) Provisional application No. 62/507,335, filed on May 17, 2017.

(51) Int. Cl.
*A61J 7/00* (2006.01)
*A61M 5/315* (2006.01)
*A61M 5/31* (2006.01)

(52) U.S. Cl.
CPC .......... *A61J 7/0007* (2013.01); *A61J 7/0053* (2013.01); *A61M 5/3129* (2013.01); *A61M 5/31511* (2013.01)

(58) Field of Classification Search
CPC ...... A61J 7/0007; A61J 7/0053; A61J 7/2096; A61J 1/20; A61M 2005/2026; A61M 2005/2451; A61M 5/30; A61M 5/31511; A61M 5/3158; A61M 5/16827; A61M 5/2066; A61M 5/284; A61M 5/2448; A61M 5/31596; A61M 5/3294; A61M 15/0028; A61M 2202/066
See application file for complete search history.

(56) References Cited

U.S. PATENT DOCUMENTS 8,038,338 B2 * 10/2011 Maleiro Vilarino ........................ A47J 43/0705 366/129

FOREIGN PATENT DOCUMENTS

WO WO-2009095077 A1 * 8/2009 .......... A61M 5/3134

* cited by examiner

*Primary Examiner* — Nathan R Price
*Assistant Examiner* — Tania Ismail
(74) *Attorney, Agent, or Firm* — Greg N. Geiser; Gutwein Law

(57) ABSTRACT

Described herein is a medication crushing, grinding, and administering device generally adapted to transform a solid pharmaceutical into a powered form for dissolving into a fluid within a syringe body. The device includes a plunger portion including the working portion of the device in the form of a blade generally extending from the plunger portion and configured for rotation. The rotating blade manipulated within an interior of the syringe body for generally breaking apart a pill within the syringe body for dispersal into a solution for administering.

2 Claims, 9 Drawing Sheets

MEDICATION CRUSHING, GRINDING, AND ADMINISTERING SYRINGE AND METHOD OF USE

CROSS REFERENCE TO RELATED APPLICATIONS

This application claims priority to U.S. Provisional Patent Application No. 62/507,335 filed 17 May 2017 to the above named inventor, and is herein incorporated by reference in its entirety.

FEDERALLY SPONSORED RESEARCH OR DEVELOPMENT

Not Applicable

SEQUENCE LISTING, A TABLE, OR A COMPUTER PROGRAM

Not Applicable

FIELD OF THE INVENTION

The invention relates generally to a syringe-like device and method of use configured for the crushing, grinding, and administering of a pharmaceutical.

BACKGROUND

Within the field of medicine, often a pharmaceutical product needs to be delivered to a patient as part of a treatment protocol. Frequently, this pharmaceutical is provided in a pill or capsule form that requires crushing for administration in a liquid form within a suspension or solution.

Typically, these pills or capsules are crushed through some type of mechanical means that exerts a grinding and crushing force. One such solution is what is known as a pill grinder. A pill grinder utilizes a pair of surfaces retained within a housing that are generally compacted or ground together to pulverize the pill between the surfaces into a powder that is retained within the housing. This traditional solution is not preferred as some medication is lost or retained within the housing due to machine inefficiencies potentially resulting in an improper dose.

Further, crushing pills or capsules within a traditional grinding device is undesired due to the potential exposure of the pharmaceutical during crushing. Accordingly, the user of the traditional device is exposed to a risk of inhalation and contact that may be harmful. Still further, this exposure can be increased depending upon the type and dosage of the pharmaceutical being crushed, including exposure to teratogenic compounds.

Therefore, these is a need in the market for an improved pill or capsule grinding device. Preferably, this device provides a generally sealed area for crushing and grinding, is automated, and easily placed into a solution or suspension for use.

SUMMARY OF THE INVENTION

The device of the present disclosure provides an improved pill crushing, grinding, and administering device and method of use. The device is comprised of a generally cylindrical hollow syringe body defining an interior cavity and configured to allow for the administration of a pill in a crushed form. The syringe body cavity allowing for the receipt of a measured volume of fluid and having a tip for the administration of a fluid mixed within the cavity. The syringe body is generally unaltered from those as are commonly found within the prior art.

A plunger portion is sized for receipt within the syringe body interior cavity and generally comprises the working portion of the device. The plunger portion having a first end opposite to a second end, wherein the distance between the first end and the second end defines a length of the plunger portion. The first end includes a gasket sized for receipt with the cavity adapted to seal and compress the contents of the cavity during a compression of the plunger portion during use.

The first end includes a retractable blade generally positioned within the gasket and wherein the blade is configured for movement away from the gasket opposite the second end and in coupled communication with a power source and motor located within the plunger body along the length and movable from a retracted to an extended position. The blade is generally rotated to slice, cut, pulverize, break-up, and distribute solid materials in the form of a pill or capsule placed within the syringe body.

The plunger portion second end includes a power switch and provides access to an internal cavity of the plunger through a cap allowing for the placement of a power source, such as a battery, to power the rotation of the blade.

In the use of the device, a user will place a pill to be crushed within the syringe body, a solution may be added, the plunger portion is placed within the syringe body, with the first portion engaged with the pill to be dispersed, wherein the blade is powered to crush, pulverize and disperse the pill into a solution or suspension within the syringe cavity.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

Figure 1:
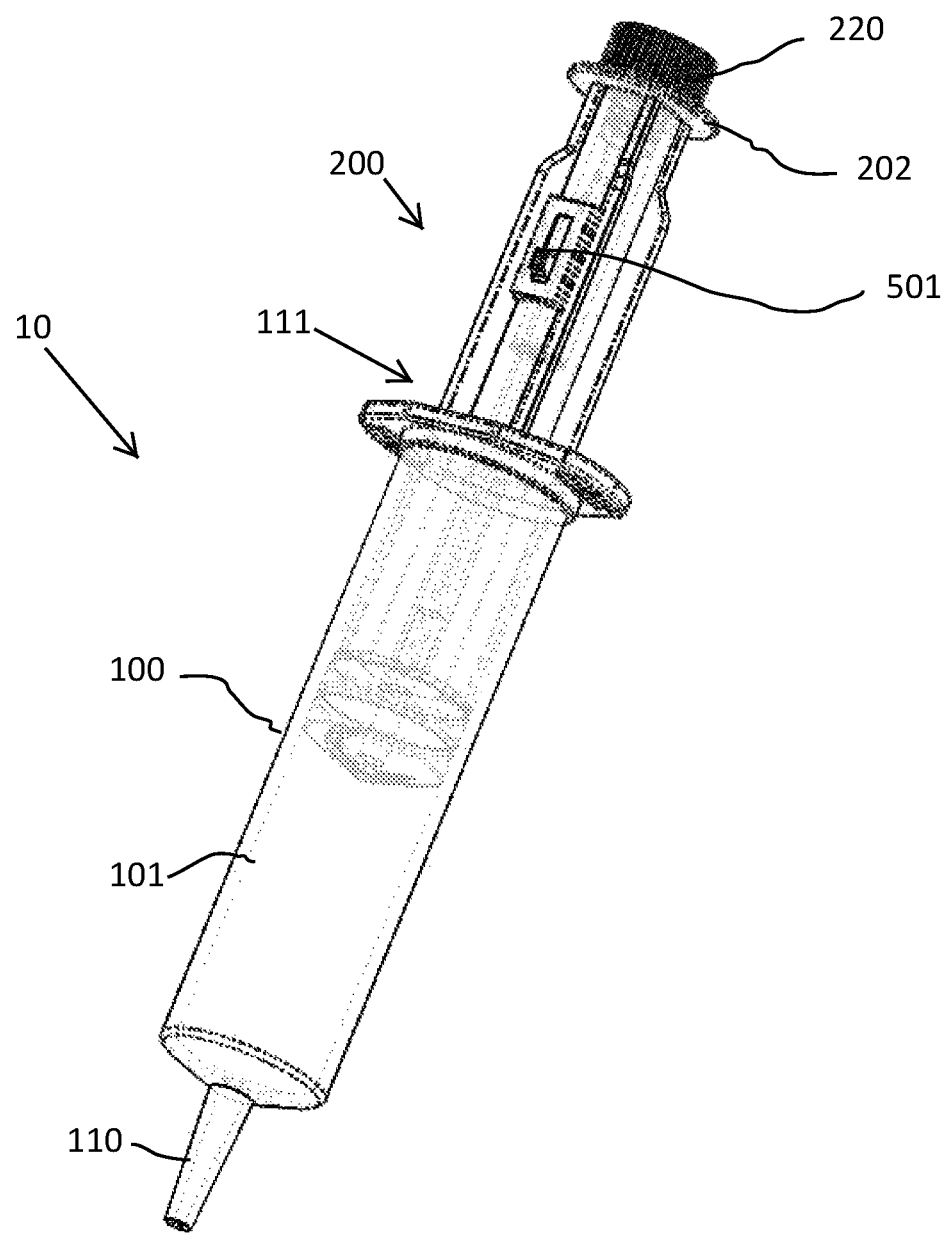
FIG. 1 shows an isometric view of the device, according to the present disclosure.

The following detailed description includes references to the accompanying drawing, which forms a part of the detailed description. The drawing shows, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the disclosure made herein.

Unless otherwise indicated, the words and phrases presented in this document have their ordinary meanings to one of skill in the art. Such ordinary meanings can be obtained by reference to their use in the art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the invention.

As used herein, the terms "front," "back," "rear," "upper," "lower," "right," and "left" in this description are merely used to identify the various elements as they are oriented in the FIGS, with "front," "back," and "rear" being relative to the apparatus. These terms are not meant to limit the elements that they describe, as the various elements may be oriented differently in various applications.

As used herein, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

The present disclosure is related to a medication crushing, grinding, administering syringe device and method for use.

The device of the present disclosure is configured to aid in the elimination of the risks associated with the potential inhalation of pill and capsule debris during grinding or crushing and increase the overall efficiency the grinding and crushing process, expanding the variety of pills that can be offered to patients.

Figure 2:
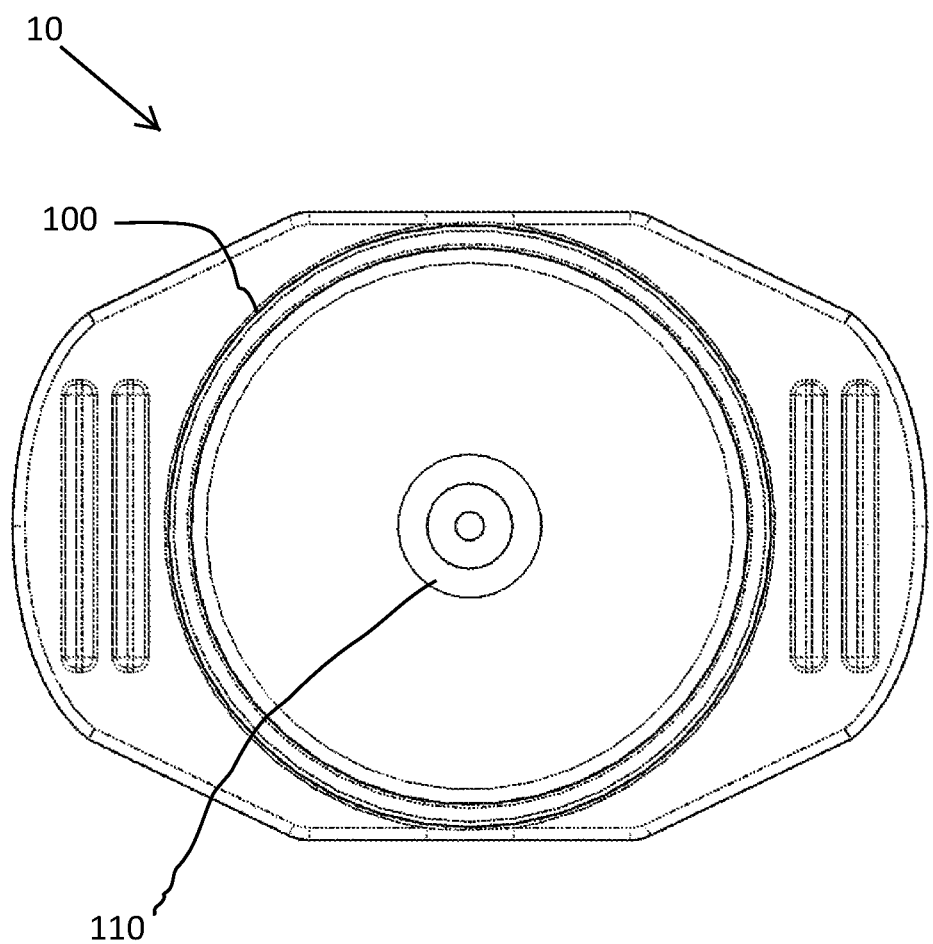
FIG. 2 shows a bottom side view of the device, according to the present disclosure.
Figure 3:
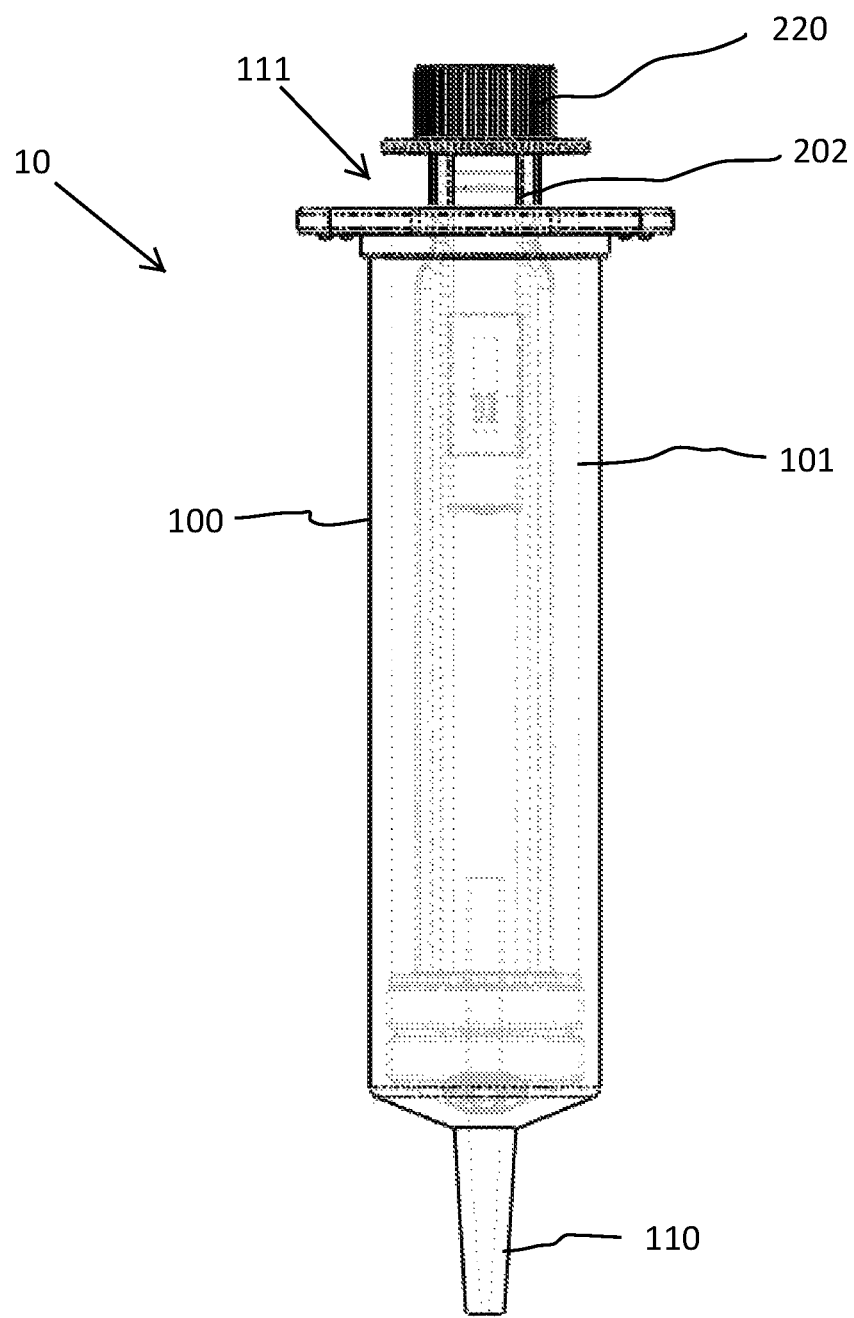
FIG. 3 shows a front side view of the device, according to the present disclosure.
Figure 4:
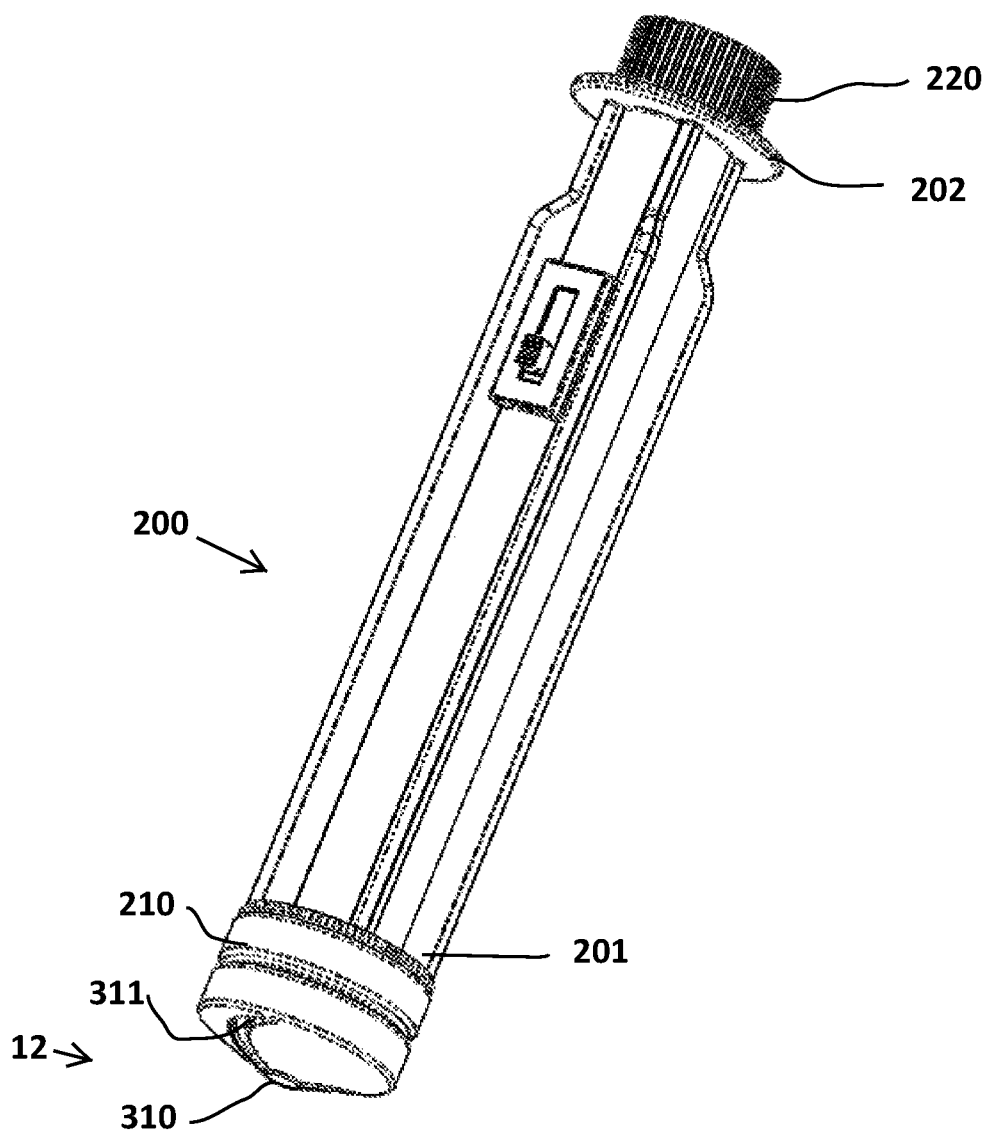
FIG. 4 shows an isometric view of the plunger portion, according to the present disclosure.
Figure 5:
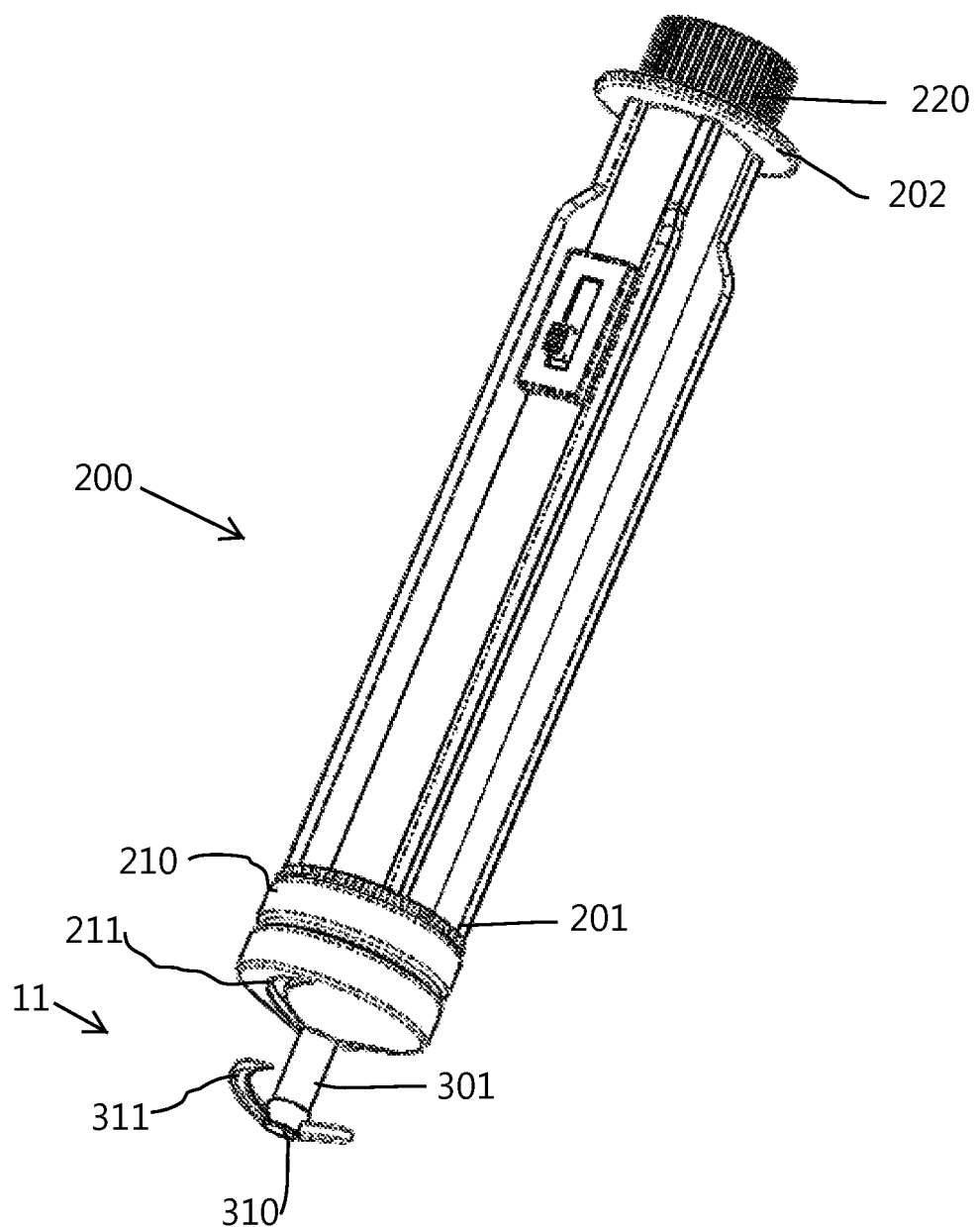
FIG. 5 shows an isometric view of the plunger portion with the blade in an extended position, according to the present disclosure.
Figure 6:
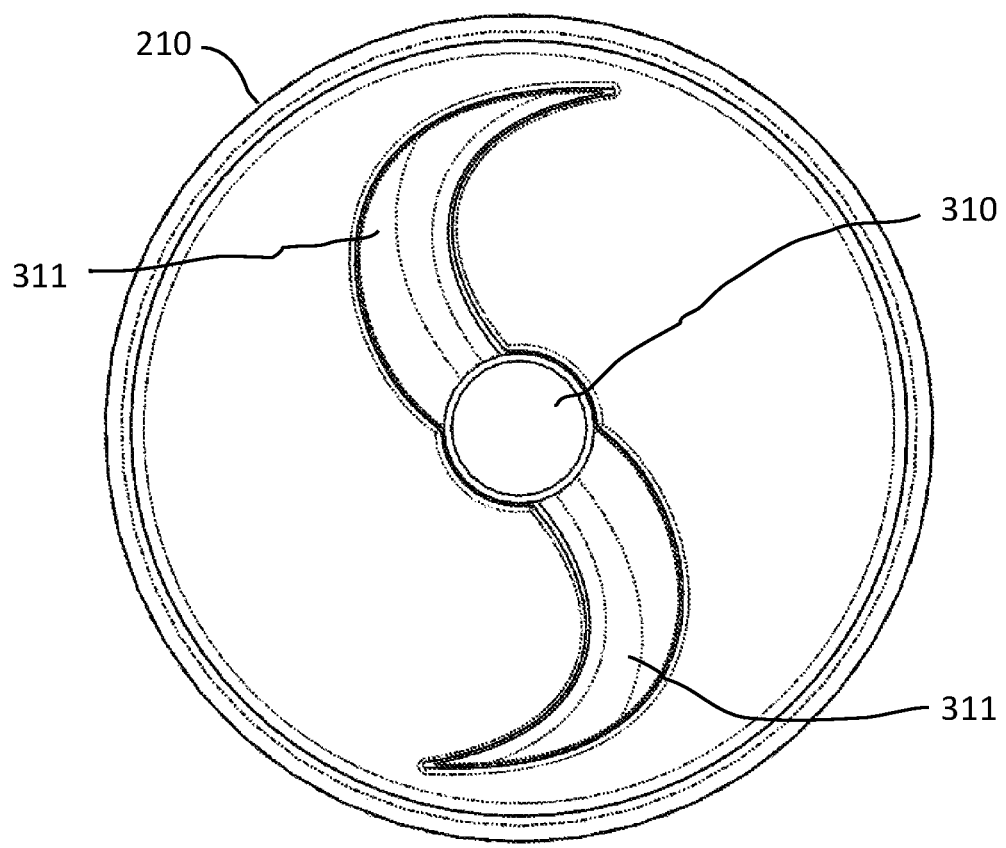
FIG. 6 shows a bottom view of the plunger portion, according to the present disclosure.
Figure 7:
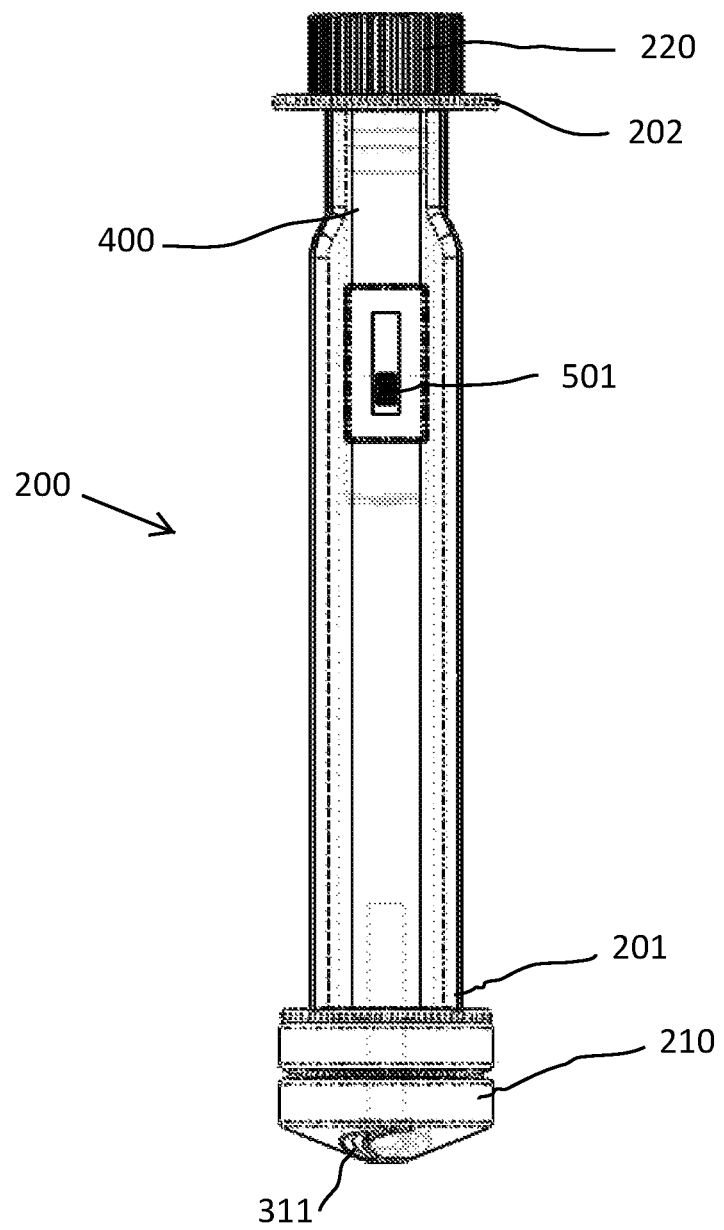
FIG. 7 shows a front side view of the plunger portion, according to the present disclosure.
Figure 8:
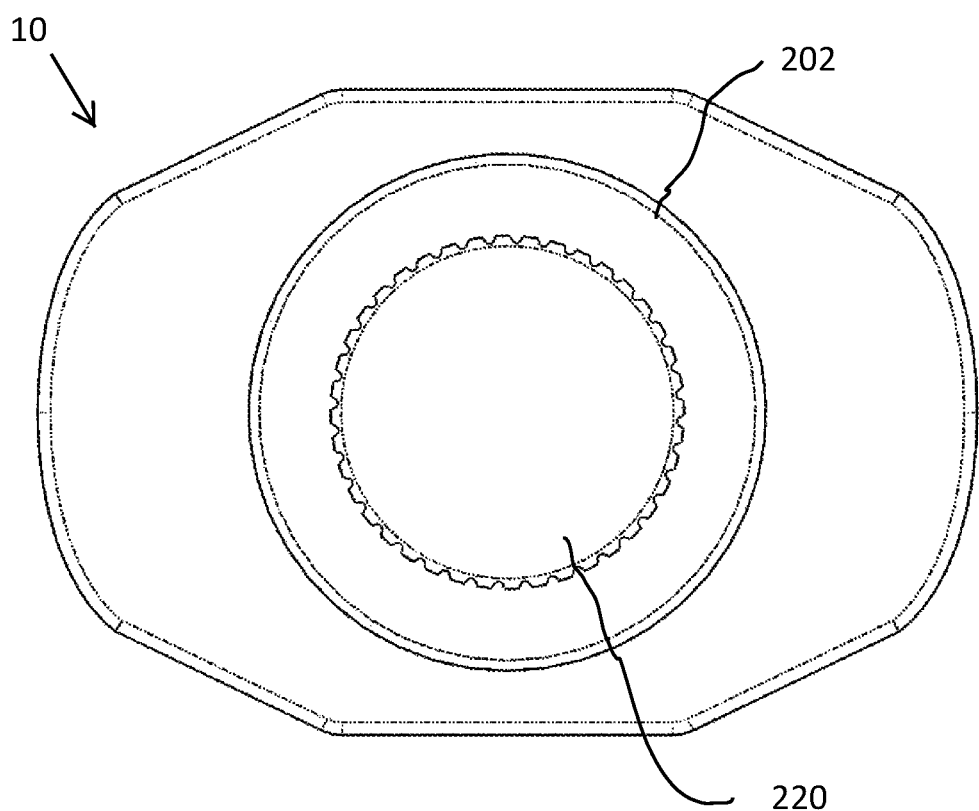
FIG. 8 shows a top side view of the device, according to the present disclosure.
Figure 9:
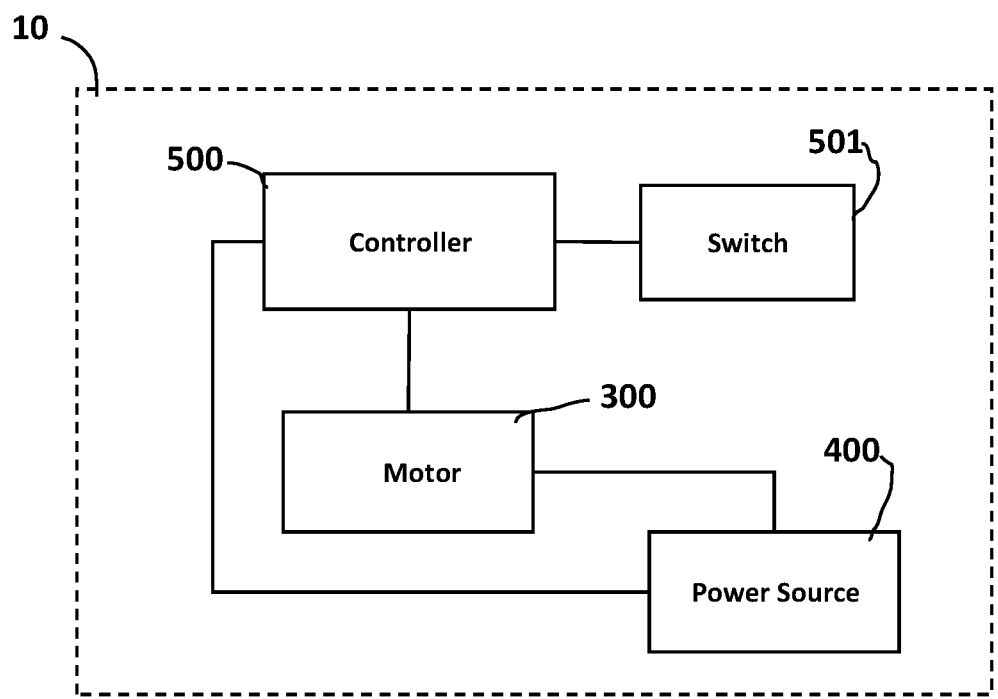
FIG. 9 is a wire frame diagram of the device, according to the present disclosure.

Referring to the figures, FIG. 1-FIG. 9 show the grinding and crushing syringe of the present disclosure and generally referred to as device 10. The device 10 is generally configured in the form of a modified syringe to crush a pill, capsule, or other solidly formed medication into a powdered form for later dissolving into a solution or suspension for administration directly from the device 10. Accordingly, the device 10 is comprised of a generally cylindrical syringe body 100 defining an interior cavity 101 for a measured volume of fluid encompassed by a tip 110 at a first end and an opening 111 at a second end opposite the first end. The tip 110 adapted for the administration of a fluid from the interior cavity 101 in fluid communication with the interior cavity 101 and generally forming a tapered conical shape extending distal the first end. Accordingly, the syringe body 100 is generally unaltered from those as are commonly found within the prior art.

A plunger portion 200 is sized for receipt within the syringe body 100 interior cavity 101 at the opening 111 of the second end and generally comprises the working portion of the device 10. The plunger portion 200 having a first end 201 opposite to a second end 202, wherein the distance between the first end 201 and the second end 202 defines a length of the plunger portion 200.

An exterior of the plunger portion 200 forms a housing defining an interior plunger cavity for the placement of various working components of the device 10. Accordingly, this interior plunger cavity generally extends the length of the plunger portion 200 and includes a motor 300, a power source 400, and a controller 500. The controller 500 coupled to the power source 400 and motor 300 to generally control the function and operation of the device. The controller 500 coupled to a switch 501 generally positioned on an external portion of the plunger portion 200 for starting and ending operation of the device 10 by engaging the motor 300.

The motor 300 of the device 10 is contained within the interior plunger cavity and configured to rotate a shaft 301. The shaft 301 movable in both a rotational direction about an axis perpendicular to the length of the plunger portion 200 and linear direction parallel to the length of the plunger portion 200. The shaft 301 having a working end 310 distal to the motor 300 coupling movable from a recessed position 12 to an extended position 11. The working end 310 comprising at least one blade 311. The blade 311 extending perpendicular to a length of the shaft 301 and including a cutting edge configured to crush, slice, chop, pulverize, break-up, and distribute solid materials and otherwise turn a solid pill, capsule, other solid material, or medication, into a powdered form. Preferably, the working end 310 includes a pair of blades 311 positioned in opposed positions on the shaft, each blade 311 of the pair of blades having an arcuate shape and a length generally corresponding to a length of a radius of the cylindrical syringe body 100.

The plunger portion 200 first end 201 includes a gasket 210 sized for receipt within the opening 111 of the interior cavity 101 of the syringe body 100 and configured to seal and compress the contents of the cavity 101 during use. The gasket 210 comprised of a resilient material to provide a flexible contact with sidewalls of the interior cavity 101 for generally expressing a fluid from within the interior cavity 101 out of the tip 110.

The gasket 210 including a recess 211 and a central aperture 212. The recess 211 generally indented into the gasket towards the second end 202 and having a size and shape corresponding to the size and shape of the blade 311 to provide a space for the blade 311 or pair of blades 311 in the recessed position 12. The central aperture 212 providing a space for the exit of the shaft 301 from the plunger portion 200 interior and allowing for the movement of the shaft 301 from the retracted 12 to extended 11 positions. The central aperture 212 generally sealing to the shaft and providing a substantially fluid tight connection to prevent the intrusion of a fluid into the plunger 200 interior during use of the device 10.

The plunger portion 200 second end 202 is adapted for manipulation by a user of the device 10, wherein the user generally pushes the first end 201 into the opening 111 and through the interior cavity 101. The second end 202 including a cap 220 providing access to the interior of the plunger portion 200 and configured for removal. The cap 220 removed for the placement of the power source 400, wherein the power source 400 can be easily removed and replaced. Preferably, the power source 400 is a battery, such as a standard sized AAA or AA battery of a suitable voltage to power the mechanisms of the device 10 during use.

In the use of the device 10, the user will place a pill to be crushed within the syringe body 100 interior space 101, a solution may be added, the plunger portion 200 first end 201 placed within the syringe body 100 opening 111 and moved to a position adjacent to the pill, the user will then power on the device 10 with the switch 501, moving the shaft 301 to the extended position 11, wherein the blade 311 is powered and rotated into an engagement with the pill to crush and disperse the pill into solution within the syringe interior cavity 101, the mixed solution is then dispersed through the tip 110 to deliver the medication to a patient.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

The invention claimed is:

1. An apparatus for crushing a pill into a powdered form, the apparatus comprising:
   a cylindrical syringe body, the cylindrical syringe body comprising:
      an interior cavity with a measured volume;
      a first end;
      a second end, the second end opposite the first end;
      a tip, the tip extending distal the first end opposite the second end, the tip in fluid communication with the interior cavity;
      an opening, the opening at the second end and providing access to the interior cavity; and
   a plunger portion, the plunger portion sized for receipt in the opening and within the interior cavity, the plunger portion comprising:
      a first end, the first end including a gasket, the gasket includes a recess, the recess sized and shaped to correspond to a blade and configured to receive the blade in a recessed position;
      a second end, the second end opposite the first end, the distance between the first end and the second end defining a length of the plunger portion;
      a power source;
      a motor coupled to the power source;
      a shaft, the shaft movable from an extended position to the recessed position and coupled to the motor for rotation at the extended position and extending parallel to the length of the plunger portion;
      a blade, the blade coupled to the shaft at an end adjacent to the first end, the blade configured for rotation upon an activation of the motor, wherein the blade crushes a pill received within the syringe body.

2. An apparatus as in claim 1, wherein the power source is removable.

* * * * *